United States Patent [19]

Robl

[11] Patent Number: 5,637,698
[45] Date of Patent: Jun. 10, 1997

[54] FUSED MULTIPLE RING LACTAMS

[75] Inventor: Jeffrey A. Robl, Newtown, Pa.

[73] Assignee: Bristol-Myers Squibb Co., Princeton, N.J.

[21] Appl. No.: 607,058

[22] Filed: Feb. 26, 1996

Related U.S. Application Data

[62] Division of Ser. No. 153,854, Nov. 18, 1993, Pat. No. 5,525,723.

[51] Int. Cl.$^6$ .................. C07D 487/14; C07D 487/16; A61K 31/55
[52] U.S. Cl. ............................................. 540/521; 514/214
[58] Field of Search ............................................ 540/521

[56] References Cited

U.S. PATENT DOCUMENTS

| | | | |
|---|---|---|---|
| 4,105,776 | 8/1978 | Ondetti et al. | 424/274 |
| 4,337,201 | 6/1982 | Petrillo | 548/413 |
| 4,374,829 | 2/1983 | Harris et al. | 424/177 |
| 4,432,971 | 2/1984 | Karanewsky et al. | 424/177 |
| 4,432,972 | 2/1984 | Karanewsky et al. | 424/177 |
| 4,460,579 | 7/1984 | Karanewsky | 424/200 |
| 4,584,294 | 4/1986 | Ruyle | 514/214 |
| 4,711,884 | 12/1987 | Karanewsky | 514/226 |
| 4,749,688 | 6/1988 | Haslanger et al. | 514/19 |
| 4,801,609 | 1/1989 | Haslanger et al. | 514/506 |
| 4,824,832 | 4/1989 | Flynn et al. | 514/214 |
| 4,873,235 | 10/1989 | Parsons et al. | 514/312 |
| 4,879,309 | 11/1989 | Doll et al. | 514/513 |
| 4,973,585 | 11/1990 | Flynn et al. | 514/214 |
| 5,061,710 | 10/1991 | Haslanger et al. | 514/266 |
| 5,075,302 | 12/1991 | Neustadt | 524/211 |
| 5,225,401 | 7/1993 | Seymour | 514/19 |
| 5,362,727 | 11/1994 | Robl | 514/214 |
| 5,504,080 | 4/1996 | Karanewsky | 514/214 |
| 5,508,272 | 4/1996 | Robl | 514/80 |
| 5,525,723 | 6/1996 | Robl | 540/521 |
| 5,552,397 | 9/1996 | Karanewsky et al. | 514/212 |

FOREIGN PATENT DOCUMENTS

| | | | |
|---|---|---|---|
| 249224 | 12/1987 | European Pat. Off. | 540/521 |
| 481522 | 4/1992 | European Pat. Off. | 540/521 |
| 524553 | 1/1993 | European Pat. Off. | 560/153 |
| 534363 | 3/1993 | European Pat. Off. | 540/521 |
| 534396 | 3/1993 | European Pat. Off. | 514/521 |
| 534492 | 3/1993 | European Pat. Off. | 514/521 |
| 595610 | 5/1994 | European Pat. Off. | 540/521 |
| 599444 | 6/1994 | European Pat. Off. | 548/521 |
| 629627 | 12/1994 | European Pat. Off. | 540/521 |
| 2207351 | 2/1989 | United Kingdom | 560/153 |
| WO93/16103 | 8/1993 | WIPO | 540/521 |
| WO94/10193 | 5/1994 | WIPO | 540/521 |
| WO94/28901 | 12/1994 | WIPO | 540/521 |

OTHER PUBLICATIONS

Flynn et al., Tetrahedron Letters, vol. 31, pp. 815–818 (1990).

Flynn et al., J. Med. Chem., vol. 36, pp. 2420–2433 (1993).

Chackalamannil et al., Bioorganic & Medicinal Chemistry Letters, vol. 2, pp. 1003–1006 (1992).

*Primary Examiner*—Robert T. Bond
*Attorney, Agent, or Firm*—Stephen B. Davis

[57] ABSTRACT

Compounds of the formula

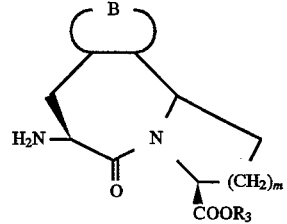

are useful as intermediates in the preparation of compounds possessing ACE and NEP inhibition activity.

5 Claims, No Drawings

FUSED MULTIPLE RING LACTAMS

RELATED APPLICATION

This application is a divisional of Ser. No. 153,854 filed Nov. 18, 1993, now U.S. Pat No. 5,525,723.

BACKGROUND OF THE INVENTION

Captopril, (S)-1-(3-mercapto-2-methyl-1-oxopropyl)-L-proline, having the structural formula

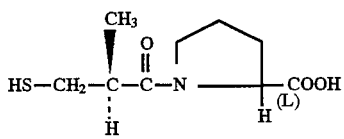

is an orally active angiotensin converting enzyme inhibitor useful for treating hypertension and congestive heart failue. See Ondetti et al. U.S. Pat. No. 4,105,776.

Enalapril, (S)-1-[N-[1-(ethoxycarbonyl)-3-phenylpropyl]-L-alanyl]-L-proline, having the structural formula

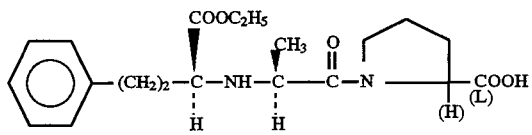

is also an orally active angiotensin converting enzyme inhibitor. Enalapril contains the L-alanyl-L-proline dipeptide. A related compound, lisinopril, also possesses oral angiotensin converting enzyme inhibitor activity and contains the L-lysyl-L-proline dipeptide. See Harris et al. U.S. Pat. No. 4,374,829.

Fosinopril sodium, (4S) -4-cyclohexyl-1-[[(R)-[(S)-1-hydroxy-2-methylpropoxy](4-phenylbutyl)-phosphinyl]acetyl]-L-proline propionate (ester), sodium salt having the structural formula

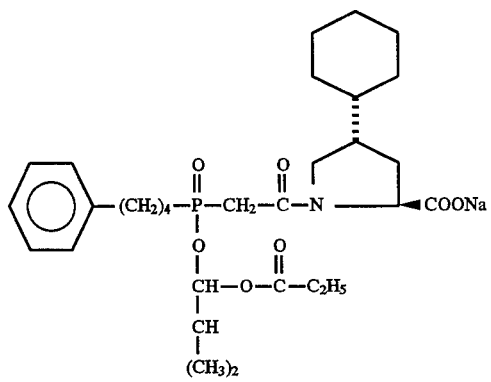

is also an orally active angiotensin converting enzyme inhibitor useful for treating hypertension. See Petrillo U.S. Pat. No. 4,337,201.

Haslanger et al. in U.S. Pat. No. 4,749,688 disclose treating hypertension by administering neutral metalloendopeptidase inhibitors alone or in combination with atrial peptides or angiotensin converting enzyme inhibitors.

Neustadt in U.S. Pat. No. 5,075,302 disclose that mercaptoacyl amino lactams of the formula

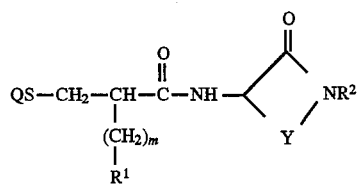

wherein Y includes propylene and butylene, $R^1$ is lower alkyl, aryl or heteroaryl, and $R^2$ is hydrogen, lower alkyl, lower alkoxy lower alkyl, aryl-lower alkyl or heteroaryl-lower alkyl are endopeptidase inhibitors. Neustadt disclose employing such compounds alone or in combination with angiotensin converting enzyme inhibitors to treat cardiovascular diseases such as hypertension, congestive heart failure, edema, and renal insufficiency.

Delaney et al. U.K. Patent 2,207,351 disclose that endopeptidase inhibitors produce diuresis and natriuresis and are useful alone or in combination with angiotensin converting enzyme inhibitors for the reduction of blood pressure. Delaney et al. include various mercapto and acylmercapto amino acids and dipeptides among their endopeptidase inhibiting compounds.

Flynn et al. in European Patent Application 481,522 disclose dual inhibitors of enkephalinase and angiotensin converting enzyme of the formulas

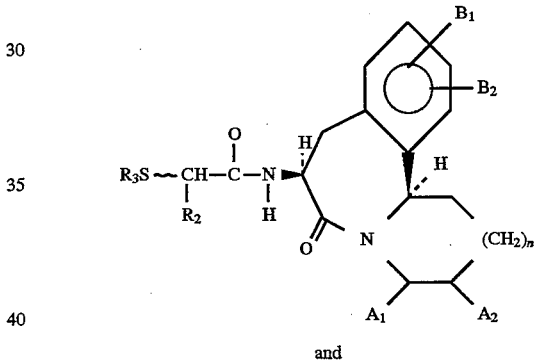

and

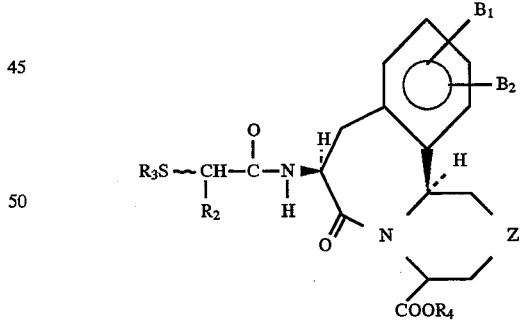

wherein n is zero or one and Z is O, S, $—NR_6—$ or

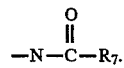

Additional tricyclic dual inhibitors are disclosed by Warshawsky et al. in European Patent Applications 534,363, 534,396 and 534,492.

Karanewsky et al. in U.S. Pat. Nos 4,432,971 and 4,432,972 disclose phosphonamidate angiotensin converting enzyme inhibitors of the formula $$\underset{OR_3}{\overset{O}{\underset{\|}{R_{21}-P}}-\overset{R_1}{\underset{|}{N}}-\overset{R_2}{\underset{|}{CH}}-\overset{O}{\underset{\|}{C}}-X}$$

wherein X is a substituted imino or amino acid or ester.

Karanewsky in U.S. Pat. No. 4,460,579 discloses angiotensin converting enzyme inhibitors including those of the formula $$\underset{OR_8}{\overset{O}{\underset{\|}{R_7-P}}-NH-X-\overset{R_1}{\underset{|}{CH}}-\overset{O}{\underset{\|}{C}}-OR_2}$$

and in U.S. Pat. No. 4,711,884 discloses angiotensin converting enzyme inhibitors including those of the formula $$\overset{O}{\underset{\|}{R_3-C}}-\underset{R_4}{\overset{|}{\underset{|}{CH}}}-NH-X-\overset{R_1}{\underset{|}{CH}}-\overset{O}{\underset{\|}{C}}-OR_2$$

wherein x is a thiazine or thiazepine.

Ruyle in U.S. Pat. No. 4,584,294 disclose angiotensin converting enzyme inhibitors of the formula

[structure with R³ on phenyl ring, R¹—CH—NH with COOR, fused to bicyclic N ring with COOR²]

Parsons et al. in U.S. Pat. No. 4,873,235 disclose angiotensin converting enzyme inhibitors of the formula

[structure with R₃ on phenyl ring, R₁—CH—NH with COOR₆, connected to N—CH—COOR₅ with R₄]

SUMMARY OF THE INVENTION

This invention is directed to novel compounds containing a fused multiple ring lactam which are useful as angiotensin converting enzyme inhibitors. Some of these compounds also possess neutral endopeptidase inhibitory activity. This invention is also directed to pharmaceutical compositions containing such selective or dual action inhibitors and the method of using such compositions. This invention is also directed to the process for preparing such novel compounds and novel intermediates.

The novel fused multiple ring lactam compounds of this invention include those compounds of the formula

[fused bicyclic lactam structure with B ring, A—NH group, N ring with (CH₂)ₘ—COOR₃]

and pharmaceutically acceptable salts thereof wherein:

A is $R_2-S-(CH_2)_n-\underset{R_{12}}{\overset{}{\underset{/}{C}}}-\overset{O}{\underset{\|}{C}}-, R_7OOC-(CH_2)_q-\underset{R_{12}}{\overset{}{\underset{/}{C}}}-\overset{O}{\underset{\|}{C}}-,$ $R_7OOC-\underset{R_1}{\overset{|}{\underset{|}{CH}}}-, \text{ or } R_4-\overset{O}{\underset{\underset{OR_5}{|}}{\overset{\|}{P}}}-;$ $R_1$ and $R_{12}$ are independently selected from hydrogen, alkyl, alkenyl, cycloalkyl, substituted alkyl, substituted alkenyl, aryl, substituted aryl, heteroaryl, cycloalkyl-alkylene-, aryl-alkylene-, substituted aryl-alkylene-, and heteroaryl-alkylene- or $R_1$ and $R_{12}$ taken together with the carbon to which they are attached complete a cycloalkyl ring or a benzofused cycloalkyl ring;

$R_2$ is hydrogen, $$\overset{O}{\underset{\|}{R_6-C}}-,$$

or $R_{11}-S-$;

$R_3$, $R_5$ and $R_7$ are independently selected from hydrogen, alkyl, substituted alkyl, aryl-$(CH_2)_p$-, substituted aryl-$(CH_2)_p$-, heteroaryl-$(CH_2)_p$-, $$-\underset{R_8}{\overset{|}{\underset{|}{CH}}}-O-\overset{O}{\underset{\|}{C}}-R_9, \text{ and } -CH_2-\overset{O}{\underset{R_{10}}{\overset{\|}{\diagup}}}\overset{O}{\diagdown};$$

$R_4$ is alkyl, cycloalkyl-$(CH_2)_p$-, substituted alkyl, aryl-$(CH_2)_p$-, substituted aryl-$(CH_2)_p$-, or heteroaryl-$(CH_2)_p$-;

$R_6$ is alkyl, substituted alkyl, cycloalkyl-$(CH_2)_p$-, aryl-$(CH_2)_p$-, substituted aryl-$(CH_2)_p$-, or heteroaryl-$(CH_2)_p$-;

$R_8$ is hydrogen, lower alkyl, cycloalkyl, or phenyl;

$R_9$ is hydrogen, lower alkyl, lower alkoxy, or phenyl;

$R_{10}$ is lower alkyl or aryl-$(CH_2)_p$-;

$R_{11}$ is alkyl, substituted alkyl, cycloalkyl$(CH_2)_p$-, aryl-$(CH_2)_p$-, substituted aryl-$(CH_2)_p$-, heteroaryl-$(CH_2)_p$-, or $-S-R_{11}$ completes a symmetrical disulfide wherein $R_{11}$ is

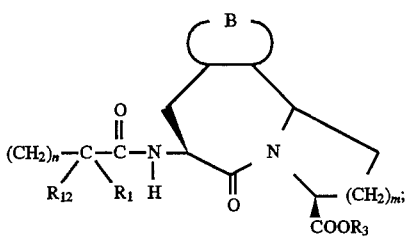

m is one or two;
n is zero or one;
q is zero or an integer from 1 to 3;
p is zero or an integer from 1 to 6;

represents an aromatic heteroatom containing ring selected from

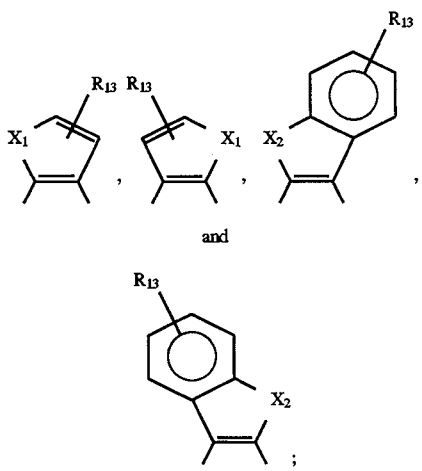

$X_1$ is S or NH;
$X_2$ is S, O, or NH; and
$R_{13}$ is hydrogen, lower alkyl, lower alkoxy, lower alkylthio, chloro, bromo, fluoro, trifluoromethyl, amino, —NH(lower alkyl), —N(lower alkyl)$_2$, or hydroxy.

DETAILED DESCRIPTION OF THE INVENTION

The term "alkyl" refers to straight or branched chain radicals having up to seven carbon atoms. The term "lower alkyl" refers to straight or branched radicals having up to four carbon atoms and is a preferred subgrouping for the term alkyl.

The term "substituted alkyl" refers to such straight or branched chain radicals of 1 to 7 carbons wherein one or more, preferably one, two, or three, hydrogens have been replaced by a hydroxy, amino, cyano, halo, trifluoromethyl, —NH(lower alkyl), —N(lower alkyl)$_2$, lower alkoxy, lower alkylthio, or carboxy.

The term "halo" refers to chloro, bromo, fluoro, or iodo.

The terms "lower alkoxy" and "lower alkylthio" refer to such lower alkyl groups as defined above attached to an oxygen or sulfur.

The term "cycloalkyl" refers to saturated rings of 3 to 7 carbon atoms with cyclopentyl and cyclohexyl being most preferred.

The term "alkenyl" refers to straight or branched chain radicals of 3 to 7 carbon atoms having one or two double bonds. Preferred "alkenyl" groups are straight chain radicals of 3 to 5 carbons having one double bond.

The term "substituted alkenyl" refers to such straight or branched radicals of 3 to 7 carbons having one or two double bonds wherein a hydrogen has been replaced by a hydroxy, amino, halo, trifluoromethyl, cyano, —NH(lower alkyl), —N(lower alkyl)$_2$, lower alkoxy, lower alkylthio, or carboxy.

The term "alkylene" refers to straight or branched chain radicals having up to seven carbon atoms, i.e. —CH$_2$—, —(CH$_2$)$_2$—, —(CH$_2$)$_3$—, —(CH$_2$)$_4$—,

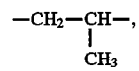

etc.

The term "aryl" refers to phenyl, 1-naphthyl, and 2-naphthyl. The term "substituted aryl" refers to phenyl, 1-naphthyl, and 2-naphthyl having a substituent selected from lower alkyl, lower alkoxy, lower alkylthio, halo, hydromy, trifluoromethyl, amino, —NH(lower alkyl), or —N(lower alkyl)$_2$, and di- and tri-substituted phenyl, 1-naphthyl, or 2-naphthyl wherein said substituents are selected from methyl, methoxy, methylthio, halo, hydroxy, and amino.

The term "heteroaryl" refers to unsaturated rings of 5 or 6 atoms containing one or two O and S atoms and/or one to four N atoms provided that the total number of hetero atoms in the ring is 4 or less. The heteroaryl ring is attached by way of an available carbon or nitrogen atom. Preferred heteroaryl groups include 2-, 3-, or 4-pyridyl, 4-imidazolyl, 4-thiazolyl, 2- and 3-thienyl, and 2- and 3-furyl. The term heteroaryl also includes bicyclic rings wherein the five or six membered ring containing O, S, and N atoms as defined above is fused to a benzene or pyridyl ring. Preferred bicyclic rings are 2- and 3-indolyl and 4- and 5-quinolinyl. The mono or bicyclic heteroaryl ring can also be additionally substituted at an available carbon atom by a lower alkyl, halo, hydroxy, benzyl, or cyclohexylmethyl. Also, if the mono or bicyclic ring has an available N-atom such N atom can also be substituted by an N-protecting group such as

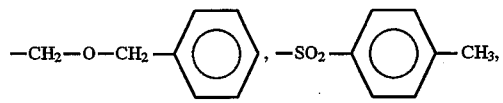

2,4-dinitrophenyl, lower alkyl, benzyl, or benzhydryl.

The compounds of formula I wherein

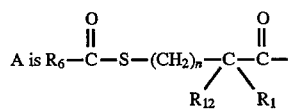

can be prepared by coupling the acylmercapto containing sidechain of the formula $$R_6-\overset{O}{\underset{\|}{C}}-S-(CH_2)_n-\underset{R_{12}}{\overset{R_1}{C}}-\overset{O}{\underset{\|}{C}}-OH \quad \text{(II)}$$

with a fused multiple ring lactam of the formula $$\underset{H_2N}{\overset{B}{\diagup}}\underset{O}{\overset{}{\diagdown}}\text{N}-(CH_2)_m\text{COOR}_3 \quad \text{(III)}$$

to give the product of formula $$R_6-\overset{O}{\underset{\|}{C}}-S-(CH_2)_n-\underset{R_{12}}{\overset{R_1}{C}}-\overset{O}{\underset{\|}{C}}-\underset{H}{N}\diagdown\overset{B}{\underset{O}{\diagup}}\text{N}-(CH_2)_m\text{COOR}_3 \quad \text{(IV)}$$

wherein $R_3$ is an easily removable ester protecting group such as methyl, ethyl, t-butyl, or benzyl. The above reaction can be performed in an organic solvent such as methylene chloride and in the presence of a coupling reagent such as 1-ethyl-3-(3-dimethylaminopropyl)carbodiimide, dicylcohexylcarbodiimide, benzotriazol-1-yloxytris (dimethylamino)phosphonium hexafluorophosphate, or carbonyldiimidazole. Alternatively, the acylmercapto carboxylic acid of formula II can be converted to an activated form prior to coupling such as an acid chloride, mixed anhydride, symmetrical anhydride, activated ester, etc.

The product of formula IV can be converted to the mercaptan product of formula I wherein $R_2$ is hydrogen and $R_3$ is hydrogen by methods known in the art. For example, when $R_6$ is methyl and $R_3$ is methyl or ethyl treatment with methanolic sodium hydroxide yields the products wherein $R_2$ and $R_3$ are hydrogen.

The products of formula I wherein $R_2$ is hydrogen can be acylated with an acyl halide of the formula $$R_6-\overset{O}{\underset{\|}{C}}-\text{halo} \quad \text{(V)}$$

wherein halo is F, Cl or Br or acylated with an anhydride of the formula $$R_6-\overset{O}{\underset{\|}{C}}-O-\overset{O}{\underset{\|}{C}}-R_6 \quad \text{(VI)}$$

to give other products of formula I wherein $R_2$ is $$R_6-\overset{O}{\underset{\|}{C}}-.$$

The products of formula I wherein $R_2$ is $-S-R_{11}$ and $R_{11}$ is alkyl, substituted alkyl, cycloalkyl-$(CH_2)_p$-, aryl-$(CH_2)_p$-, substituted aryl-$(CH_2)_p$-, or heteroaryl-$(CH_2)_p$- can be prepared by reacting the products of formula I wherein $R_2$ is hydrogen with a sulfonyl compound of the formula $$H_3C-SO_2-S-R_{11} \quad \text{(VII)}$$

in an aqueous alcohol solvent to yield the desired products. The compounds of formula VII are known in the literature or can be prepared by known methods, see for example, Smith et al., Biochemistry, 14, p 766–771 (1975).

The symmetrical disulfide products of formula I can be prepared by direct oxidation of the product of formula I wherein $R_2$ is hydrogen with iodine as note, for example, Ondetti et al. U.S. Pat. No. 4,105,776.

The acylmercapto sidechain compounds of formula II wherein $R_{12}$ is hydrogen are described in the literature. See, for example, Ondetti et al. U.S. Pat. Nos. 4,105,776 and 4,339,600, Haslanger et al. U.S. Pat. No. 4,801,609, Delaney at al. U.S. Pat. No. 4,722,810, etc.

The acylmercapto sidechain compounds of formula II wherein $R_1$ and $R_{12}$ are both other than hydrogen and n is zero can be prepared by reacting the substituted carboxylic acid of the formula $$HC-\underset{R_{12}}{\overset{R_1}{C}}-\overset{O}{\underset{\|}{C}}-OH \quad \text{(VIII)}$$

with bis[(4-methoxy)phenyl]methyldisulfide in the presence of lithium diisopropylamide to give the compound of the formula $$H_3CO-\text{\Large\textcircled{ }}-H_2C-S-\underset{R_{12}}{\overset{R_1}{C}}-\overset{O}{\underset{\|}{C}}-OH. \quad \text{(IX)}$$

Treatment of the compound of formula IX with strong acid such as trifluoromethanesulfonic acid removes the methoxybenzyl protecting group and is followed by acylation with the acyl halide of formula V or anhydride of formula VI to give the compound of formula II wherein $R_1$ and $R_{12}$ are both other than hydrogen and n is zero.

The acylmercapto sidechain compounds of formula II wherein $R_1$ and $R_{12}$ are both other than hydrogen and n is one can be prepared by reacting the substituted carboxylic acid of the formula $$HO-CH_2-\underset{R_{12}}{\overset{R_1}{C}}-\overset{O}{\underset{\|}{C}}-OH \quad \text{(X)}$$

with para-toluenesulfonyl chloride in pyridine to give the lactone of the formula $$\underset{O}{\overset{O}{\diagup\diagdown}}\underset{R_{12}}{\overset{R_1}{\diagdown\diagup}} \quad \text{(XI)}$$

Treatment of the lactone of formula XI with a cesium thioacid of the formula $$Cs-S-\overset{O}{\underset{\|}{C}}-R_6 \quad \text{(XII)}$$

in the presence of dimethylformamide yields the desired acylmercapto sidechain of formula II wherein $R_1$ and $R_{12}$ are both other than hydrogen and n is one.

The compounds of formula I wherein A is $$R_7OOC-(CH_2)_q-\underset{R_{12}}{\overset{R_1}{C}}-\overset{\overset{O}{\|}}{C}-,$$

can be prepared by coupling the acid of the formula $$R_7OOC-(CH_2)_q-\underset{R_{12}}{\overset{R_1}{C}}-\overset{\overset{O}{\|}}{C}-OH \quad (XIII)$$

wherein $R_7$ is an ester protecting group with the fused multiple ring lactam of formula III in the presence of a coupling reagent as defined above to give the product of the formula (XIV)

[Structure showing $R_7OOC-(CH_2)_q-C(R_{12})(R_1)-C(=O)-N(H)$ linked to a bicyclic lactam with B ring, N, (CH$_2$)$_m$, and COOR$_3$]

Alternatively, the acid of formula XIII can be converted to an activated form such as an acid chloride prior to the coupling reaction.

The acids of formula XIII are described by Warshawsky et al. in European Patent Application 534,396 and 534,492.

The compounds of formula I wherein A is $$R_7OOC-\underset{R_1}{\overset{}{C}H}-$$

can be prepared by reacting a keto acid or ester of the formula $$R_7O-\overset{\overset{O}{\|}}{C}-\overset{\overset{O}{\|}}{C}-R_1 \quad (XV)$$

with fused multiple ring lactam of formula III under reducing conditions to give the product of the formula (XVI)

[Structure showing $R_7O-C(=O)-CH(R_1)-N(H)$ linked to bicyclic lactam with B, N, (CH$_2$)$_m$, COOR$_3$]

The keto acids and esters of formula XV are described in the literature. See, for example, Ruyle U.S. Pat. No. 4,584,294 and Parsons et al. U.S. Pat. No. 4,873,235.

Alternatively, the fused multiple ring lactam compound formula III can be reacted with a triflate of the formula $$R_7O-\overset{\overset{O}{\|}}{C}-\underset{}{\overset{OSO_2CF_3}{\overset{|}{C}H}}-R_1 \quad (XVII)$$

to give the product of formula XVI.

The compounds of formula I wherein A is $$R_4-\overset{\overset{O}{\|}}{\underset{\underset{OR_5}{|}}{P}}-$$

can be prepared by coupling a phosphonochloridate of the formula $$R_4-\overset{\overset{O}{\|}}{\underset{\underset{OR_5}{|}}{P}}-Cl \quad (XVIII)$$

wherein $R_5$ is lower alkyl or benzyl with a fused multiple ring lactam of formula III to give the product of the formula (XIX)

[Structure showing $R_4-P(=O)(OR_5)-N(H)$ linked to bicyclic lactam with B, N, (CH$_2$)$_m$, COOR$_3$]

Preferably, the compound of formula III is in its hydrochloride salt form and $R_3$ is lower alkyl or benzyl. The $R_3$ and $R_5$ ester protecting groups can be removed, for example, by hydrogenation to give the corresponding products of formula I wherein $R_3$ and $R_5$ are hydrogen.

The phosphonochloridates of formula XVIII are known in the literature. See, for example, Karanewsky et al. U.S. Pat. Nos 4,432,971 and 4,432,972 and Karanewsky U.S. Pat. No. 4,460,579.

The ester products of formula I wherein $R_5$ or $R_7$ is $$-\underset{R_8}{\overset{}{C}H}-O-\overset{\overset{O}{\|}}{C}-R_9 \quad \text{or} \quad -CH_2-\underset{}{\overset{O\diagdown\diagup O}{\underset{R_{10}}{\diagdown=\diagup}}}$$

[with acetal/dioxolene type structure]

can be prepared by treating the corresponding compounds of formula I wherein $R_5$ or $R_7$ is hydrogen and $R_3$ is an ester protecting group with a compound of the formula $$L-\underset{R_8}{\overset{}{C}H}-O-\overset{\overset{O}{\|}}{C}-R_9 \quad \text{or} \quad L-CH_2-\underset{R_{10}}{\overset{O\diagdown\diagup O}{\diagdown=\diagup}} \quad (XX)$$

wherein L is a leaving group such as chloro, bromo, or tolylsulfonyloxy followed by removal of the $R_3$ ester protecting group.

The ester products of formula I wherein $R_3$ is

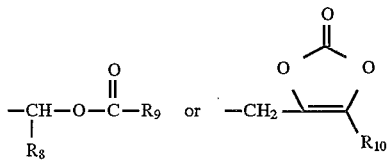

can be prepared by treating the corresponding compounds of formula I wherein $R_3$ is hydrogen and $R_2$ is

with a compound of formula XX.

The fused multiple ring lactams of formula III can be prepared according to the following process which also forms part of this invention. An N-protected carboxylic acid of the formula

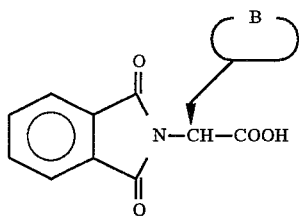

can be coupled with the amino acid ester of the formula

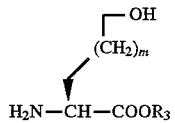

to give the compound of the formula

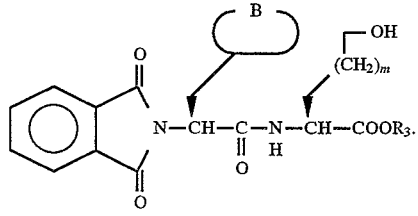

This reaction can be performed in the presence of a coupling reagent as defined above.

The alcohol of formula XXIII can be converted to the corresponding aldehyde such as by treatment with 4-methylmorpholine N-oxide and tetrapropyl ammonium perruthenate or treatment with oxalyl chloride, dimethylsulfoxide, and triethylamine. This aldehyde can then be cyclized by treatment with a strong acid such as trifluoroacetic acid or trifluoroacetic acid followed by trifluoromethanesulfonic acid to give the compound of the formula

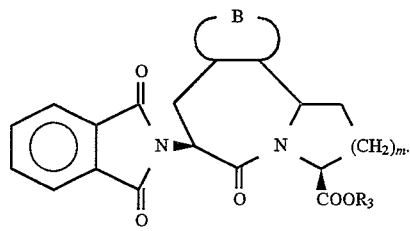

Alternatively, the N-protected carboxylic acid of the formula XXI can be coupled with the amino acid ester of the formula

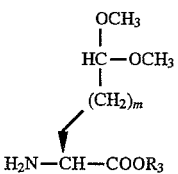

to give the compound of the formula

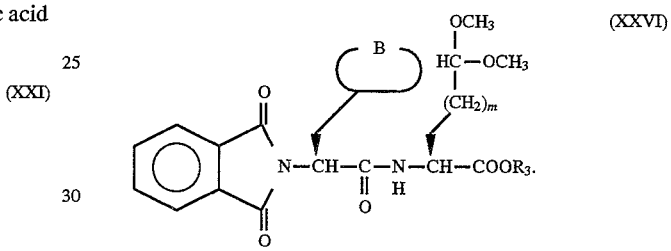

The compound of formula XXVI can be cyclized by treatment with strong acid such as trifluoroacetic acid or trifluoroacetic acid followed by trifluoromethanesulfonic acid to give the compound of formula XXIV.

Treatment of compound XXIV with hydrazine monohydrate removes the N-phthalimido protecting group and gives the fused multiple ring lactam of formula III.

The compounds of formula I contain three asymmetric centers in the fused multiple ring lactam portion of the structure with an additional center possible in the side chain. While the optically pure form of the fused multiple ring lactam described above is preferred, all such forms are within the scope of this invention. The above described processes can utilize racemates, enantiomers, or diastereomers as starting materials. When diastereomeric compounds are prepared, they can be separated by conventional chromatographic or fractional crystallization methods. Preferably, the hydrogen attached to the bridgehead carbon is in the orientation shown below

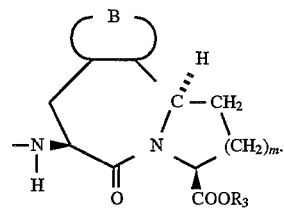

The compounds of formula I wherein $R_3$, $R_5$ and/or $R_7$ are hydrogen can be isolated in the form of a pharmaceutically acceptable salt. Suitable salts for this purpose are alkali metal salts such as sodium and potassium, alkaline earth metal salts such as calcium and magnesium, and salts derived from amino acids such as arginine, lysine, etc. These salts are obtained by reacting the acid form of the compound with an equivalent of base supplying the desired ion in a medium in which the salt precipitates or in aqueous medium and then lyophilizing.

Preferred compounds of this invention are those wherein:

A is

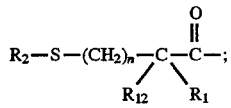

$R_2$ is hydrogen,

or $R_{11}$—S—;

$R_3$ is hydrogen or lower alkyl of 1 to 4 carbons;

n is zero or one;

$R_{12}$ is hydrogen;

$R_{11}$ is lower alkyl of 1 to 4 carbons;

$R_1$ is aryl-$CH_2$—, substituted aryl-$CH_2$—, heteroaryl-$CH_2$—, cycloalkyl-$CH_2$— wherein the cycloalkyl is of 5 to 7 carbons, or straight or branched chain alkyl of 1 to 7 carbons;

$R_6$ is lower alkyl of 1 to 4 carbons or phenyl;

m is one or two; and

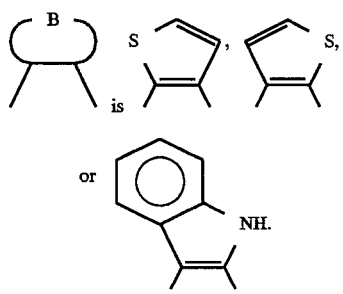

Most preferred are the above compounds wherein:

$R_2$ is hydrogen or

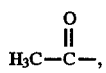

especially hydrogen;

$R_3$ is hydrogen;

n is zero;

$R_1$ is benzyl; and m is two.

The compounds of formula I wherein A is

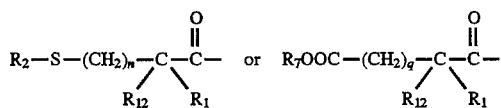

are dual inhibitors possessing the ability to inhibit angiotensin converting enzyme and neutral endopeptidase. The compounds of formula I wherein A is

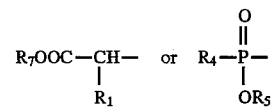

are selective inhibitors possessing the ability to inhibit the angiotensin converting enzyme. Thus, all of the compounds of formula I including their pharmaceutically acceptable salts are useful in the treatment of physiological conditions in which angiotensin converting enzyme inhibitors have been shown to be useful. Such conditions include disease states characterized by abnormalities in blood pressure, intraocular pressure, and renin including cardiovascular diseases particularly hypertension and congestive heart failure, glaucoma, and renal diseases such as renal failure. The dual inhibitors are also useful in the treatment of physiological conditions in which neutral endopeptidase inhibitors have been shown to be useful. Such conditions also include cardiovascular diseases particularly hypertension, hyperaldosteronemia, renal diseases, glaucoma, as well as the relief of acute or chronic pain. Thus, the compounds of formula I are useful in reducing blood pressure and the dual inhibitors of formula I are additionally useful for this purpose due to their diuresis and natriuresis properties. The compounds of formula I including their pharmaceutically acceptable salts can be administered for these effects to a mammalian host such as man at from about 1 mg. to about 100 mg. per kg. of body weight per day, preferably from about 1 mg. to about 50 mg. per kg. of body weight per day. The compounds of formula I are preferably administered orally but parenteral routes such as subcutaneous, intramuscular, and intravenous can also be employed as can topical routes of administration. The daily dose can be administered singly or can be divided into two to four doses administered throughout the day.

The inhibitors of formula I can be administered in combination with human ANF 99–126. Such combination would contain the inhibitor of formula I at from about 1 to about 100 mg. per kg. of body weight and the human ANF 99–126 at from about 0.001 to about 0.1 mg. per kg. of body weight.

The inhibitors of formula I can be administered in combination with other classes of pharmaceutically active compounds. For example, a calcium channel blocker, a potassium channel activator, a cholesterol reducing agent, etc.

The inhibitors of formula I or a pharmaceutically acceptable salt thereof and other pharmaceutically acceptable ingredients can be formulated for the above described pharmacetical uses. Suitable compositions for oral administration include tablets, capsules, and elixirs, and suitable compositions for parenteral administration include sterile solutions and suspensions. Suitable compositions for treating glaucoma also include topical compositions such as solutions, ointments, and solid inserts as described in U.S. Pat. No. 4,442,089. About 10 to 500 mg. of active ingredient is compounded with physiologically acceptable vehicle, carrier, excipient, binder, preservative, stabilizer, flavoring, etc., in a unit dose form as called for by accepted pharmaceutical practice.

The following examples are illustrative of the invention. Temperatures are given in degrees centigrade. Thin layer chromatography (TLC) was performed in silica gel unless otherwise stated.

EXAMPLE 1

[4S-[4α,7α(R*),13bβ]]-1,3,4,6,7,8,13,13b-Octahydro-6-oxo-7-[(2-mercapto-1-oxo-3-phenylpropyl)amino]-2H-pyrido[1',2':1,2]azepino[3,4-b]indole-4-carboxylic acid a) N-Phthalimido-L-tryptophan,dicyclohexylamine salt A slurry of L-tryptophan (15.0 g., 73.4 mmol.) and sodium carbonate (7.785 g, 73.4 mmol.) in water (200 ml.) was stirred at room temperature for 15 minutes, then treated with N-carbethoxyphthalimide (16.098 g., 73.4 mmol.). The non-homogeneous solution became yellow immediately. After stirring for 2 hours, the clear yellow solution was cooled to 0° C. and acidified with 6 N hydrochloric acid. The resulting solid was collected by filtration and washed with water. The solid was dissolved in ethyl acetate and washed with water and brine, then dried (sodium sulfate), filtered and stripped to give a yellow oil/foam. The foam was flash chromatographed (Merck silica gel, 5% acetic acid in ethyl acetate) to give the slightly impure desired free acid as a yellow oil. The oil was dissolved in ethyl acetate/ethyl ether and treated with dicyclohexylamine (14.5 ml.) to give pure title compound as a yellow powder (18.955 g.); m.p. 145°–148° (decomp.) TLC: (5% acetic acid in ethyl acetate) $R_f$=0.57.

b) N-(N-Phthalimido-L-tryptophyl)-6-hydroxy-L-norleucine, methyl ester

Hydrogen chloride gas was bubbled in a slurry of 6-hydroxy-L-norleucine [prepared as described by Bodanszky et al., J. Med. Chem., 21, p. 1030–1035 (1978), 1.00 g., 6.9 mmol.] in dry methanol (35 ml.) until the mixture became homogeneous and began to reflux. The solution was then let cool and was stirred at room temperature for 2.5 hours. The methanol was removed by rotary evaporation and the residue was azeotroped twice with toluene to give crude 6-hydroxy-L-norleucine, methyl ester hydrochloride as a gum. Meanwhile, the dicyclohexylamine salt product from part (a) (3.506 g., 6.8 mmol.) was partitioned between 5% potassium bisulfate and ethyl acetate. The ethyl acetate extract was washed with additional 5% potassium bisulfate and brine, then dried (sodium sulfate), filtered and stripped to give N-phthalimido-L-tryptophan as the free acid.

The above crude 6-hydroxy-L-norleucine, methyl ester, hydrochloride was dissolved in dimethylformamide (6 ml.) and methylene chloride (25 ml.) and treated with 4-methylmorpholine (1.30 ml., 1.20 g., 11.8 mmol.). The solution was cooled to 0° C. and treated with N-phthalimido-L-tryptophan followed by hydroxybenzotriazole (925 mg., 6.8 mmol.) and 1-ethyl-3-(3-dimethylaminopropyl)carbodiimide hydrochloride (1.438 g., 7.5 mmol.). The mixture was stirred at 0° C. for 0.5 hour and then at room temperature for 2.5 hours. The solution was partitioned between ethyl acetate and water and the organic layer was washed successively with 0.5 N hydrochloric acid, water, 5% sodium bicarbonate, and brine, then dried (sodium sulfate), filtered and stripped to give 3.06 g., of title product as a yellow foam. TLC: (ethyl acetate) $R_f$=0.35.

c) N-(N-Phthalimido-L-tryptophyl)-6-oxo-L-norleucine, methyl ester

To a pre-dried (magnesium sulfate) solution of 4-methylmorpholine N-oxide (760 mg., 6.5 mmol.) in methylene chloride (90 ml.) was added the product from part (b) (2.065 g., 4.3 mmol.), dry 4 A molecular sieves (10 g.) and tetrapropyl ammoniumperruthenate (85 mg.). The mixture was stirred at room temperature and was charged with additional tetrapropyl ammoniumperruthenate (35 mg.) after 1, 2, and 3 hours of stirring. After 3.5 hours, the dark mixture was diluted with ethyl acetate and filtered through a short plug of Merck silica gel. The filtrate was stripped and the residue was flash chromatographed (Merck silica gel, 20:80-hexanes:ethyl acetate) to give 1.160 g., of title product as a yellow foam. TLC (ethyl acetate) $R_f$=0.49.

d) [4S-[4α,7α,13bα]]-1,3,4,6,7,8,13,13b-Octahydro-6-oxo-7-phthalimido-2H-pyrido[1',2':1,2]azepino[3,4-b]indole-4-carboxylic acid, methyl ester A solution of the product from part (c) (990 mg., 2.08 mmol.) was gently refluxed in a solution of methylene chloride (26 ml.) and trifluoroacetic acid (240 µl) for 3.5 hours. The cooled solution was washed with saturated sodium bicarbonate, dried (sodium sulfate), filtered and stripped. The residue was flash chromatographed (Merck silica gel, 12% ethyl acetate in methylene chloride) to give a solid. Recrystallization from ethyl ether/methylene chloride afforded 499 mg. of the desired product as a crystalline light yellow solid; m.p. 185° C. (decomp.); $[\alpha]_D$=−117.2° (c=0.8, chloroform). TLC (20% ethyl acetate in methylene chloride) $R_f$=0.39.

e) [4S-[4α,7α,13b,βB]]-1,3,4,6,7,8,13,13b-Octahydro-7-amino-6-oxo-2H-pyrido[1',2':1,2]azepino[3,4-b]indole-4-carboxylic acid, methyl ester A slurry of the product from part (d) (570 mg., 1.24 mmol.) in methanol (5 ml.) was treated with hydrazine monohydrate (133 µl., 129 mg., 2.6 mmol.). Slight heating was neccessary to effect a homogeneous solution. After stirring at room temperature for 15 hours, the mixture (thick with precipitate) was stirred with 16 ml. of 0.5 N hydrochloric acid at 0° C. for 2.5 hours. The solution was filtered and the solid was washed with water. The filtrate was washed with ethyl acetate, made basic with 1 N sodium hydroxide and subsequently extracted twice with methylene chloride. The pooled methylene chloride extracts were dried (sodium sulfate), filtered and stripped to afford the product as a solid (145 mg.). The original aqueous insoluble precipitate was partially dissolved in methanol and partitioned with vigorous shaking between ethyl acetate and 0.5 N hydrochloric acid. The aqueous layer was separated and made basic with 2 N sodium hydroxide and subsequently extracted twice with methylene chloride. The pooled methylene chloride extracts were dried (sodium sulfate), filtered and stripped to give additional desired product (approximately 200 mg.). The isolated solids were pooled, taken up in methylene chloride, concentrated and triturated with ethyl ether to give 319 mg. of title compound as a white solid; m.p. 204°–206° C. (decomp.). $[\alpha]_D$=−30.3° (c=0.5, chloroform). TLC (8:1:1, methylene chloride:acetic acid:methanol) $R_f$=0.35.

) (S)-2-(Acetylthio)benzenepropanoic acid, dicyclohexylamine salt

Sodium nitrite (10.3 g., 280 mmol.) was added to a solution of D-phenylalanine (30.0 g., 181 mmol.) and potassium bromide (73.5 g.) in sulfuric acid (2.5 N, 365 ml.) over a period of one hour while maintaining the temperature of the reaction mixture at 0° C. The mixture was stirred for an additional hour at 0° C. and then for one hour at room temperature. The reaction solution was extracted with ether, the ether was back extracted with water, and the ether layer was dried over sodium sulfate. Ether was removed in vacuo, and distillation of the oily residue afforded 25.7 g. of (R)-2-bromo-3-benzenepropanoic acid; b.p. 141° (0.55 mm of Hg.); $[\alpha]_D$=+14.5° (c=2.4, chloroform).

A mixture of thioacetic acid (7 ml., 97.9 mmol.) and potassium hydroxide (5.48 g., 97.9 mmol.) in acetonitrile (180.5 ml.) was stirred under argon at room temperature for 1¾ hours. The mixture was cooled in an ice-bath, and a solution of (R)-2-bromo-3-benzenepropanoic acid (20.4 g., 89 mmol.) in acetonitrile (20 ml.) was added over a ten minute period. The reaction was stirred under argon at room temperature for 5 hours, filtered, and the acetonitrile was removed in vacuo. The oily residue was redissolved in ethyl acetate and washed with 10% potassium bisulfate and water. Removal of the ethyl acetate in vacuo afforded 19.6 g. of crude product. The crude product was purified via its dicyclohexylamine salt using isopropyl ether as solvent for crystallization. An analytical sample of (S)-2-(acetylthio) benzenepropanoic acid, dicyclohexylamine salt was prepared by recrystallization from ethyl acetate; m.p. 146°–147°; $[\alpha]_D$=−39.6° (c=1.39, chloro form).

Anal. calc'd. for $C_{11}H_{12}O_3S \cdot C_{12}H_{23}N$: C,68.11; H,8.70; N,3.45; S,7.91

Found: C,67.93; H,8.71; N,3.37; S,7.94.

g) [4S-[4α,7α(R*),13bβ]]-1,3,4,6,7,8,9,13,13b-Octahydro-7-[[2-(acetylthio)-1-oxo-3-phenylpropyl]amino]-6-oxo-2H-pyrido[1',2':1,2]azepino[3,4-b]indole-4-carboxylic acid, methyl ester The dicyclohexylamine salt from part (f) (450 mg., 1.11 mmol.) was partitioned between ethyl acetate and 5% potassium bisulfate. The ethyl acetate layer was washed with water and brine, then dried (sodium sulfate), filtered and stripped to give the free acid as a colorless oil. A solution of the acid and the product from part (e) (316 mg., 0.965 mmol.) in dry methylene chloride (11 ml.) was treated with triethylamine (149 µl., 108 mg., 1.07 mmol.). The mixture was cooled to 0° C. and subsequently treated with benzotriazol-1-yloxy-tris(dimethylamino) phosphonium hexafluorophosphate (449 mg., 1.02 mmol.). After stirring at 0° C. for 1 hour and at room temperature for 4.5 hours, the mixture was diluted with ethyl acetate and washed successively with 0.5 N hydrochloric acid, water, and saturated sodium bicarbonate/brine. The ethyl acetate layer was dried (sodium sulfate), filtered and stripped and the residue was flash chromatographed (Merck silica gel, 65:35-ethyl acetate:hexanes) to give 462 mg. of title product as a white foam. TLC (70:30, ethyl acetate:hexane) $R_f$=0.39.

h) [4S-[4α,7α(R*),13bβ]]-1,3,4,6,7,8,13,13b-Octahydro-6-oxo-7-[(2-mercapto-1-oxo-3-phenylpropyl)amino]-2H-pyrido[1',2':1,2]azepino[3,4b]indole-4-carboxylic acid A solution of the product from part (g) (444 mg., 0.83 mmol.) in methanol (9 ml., deoxygenated via argon bubbling) and tetrahydrofuran (2 ml.) was treated with 1 N sodium hydroxide (10 ml., deoxygenated via argon bubbling) and the mixture was stirred at room temperature with argon bubbling. Additional methanol and tetrahydrofuran were added periodically to replace that lost by evaporation. After 1.5 hours, the mixture was acidified with 1 N hydrochloric acid (15 ml.), diluted with water, and extracted with ethyl acetate. The ethyl acetate extract was washed with brine, dried (sodium sulfate), filtered, and stripped to give a pale yellow residue. The residue was flash chromatographed (Merck silica gel, 1% acetic acid in ethyl acetate). The fractions containing the desired product were pooled, stripped, and azeotroped twice with ethyl acetate. The resulting oil was dissolved in a small amount of ethyl acetate and ethyl ether and triturated with hexane. The resulting foam was collected by filtration and dried in vacuo to give 266 mg, of title product as a hard white foam; $[α]_D$=+15.9° (c=0.5, chloroform). TLC (1% acetic acid in ethyl acetate) $R_f$=0.39. HPLC: YMC S3 ODS column (6.0×150 mm); eluted with 40% A: 90% water-10% methanol-0.2% phosphoric acid and 60% B: 10% water-90% methanol-0.2% phosphoric acid; flow rate 1.5 ml/min detecting at 220 nm; $t_R$=20.46 min indicates a purity of 96.3%.

Anal. calc'd. for $C_{26}H_{27}N_3O_4S \cdot 0.7 H_2O$: C, 63.71; H, 5.84; N, 8.57; S, 6.54

Found: C, 63.61; H, 5.94; N, 8.23; S, 6.32.

EXAMPLE 2

[5S-[5α(R*),8α,11aβ]]-5,6,9,10,11,11a-Hexahydro-5-[(2-mercapto-1-oxo-3-phenylpropyl)amino]-6-oxo-4H,8H-pyrido[1,2-a]thieno[3,2-c]azepine-8-carboxylic acid a) N-Phthalimido-3-(2-thienyl)-L-alanine 3-(2-Thienyl)-L-alanine(2.24 g., 13.1 mmol.) was suspended in water/p-dioxane (20 ml./10 ml.) at room temperature under argon. Sodium carbonate (1.39 g.) was added and the mixture was stirred until homogeneous. N-Carbethoxyphthalimide (2.87 g.) was added, and the resulting mixture was stirred for 4.5 hours and then cooled to 0° C. The pH was adjusted to 1.5 with 6 N hydrochloric acid and the mixture was extracted with ethyl acetate. The organic layer was washed successively with 10% potassium bisulfate and brine, dried (sodium sulfate), filtered, and concentrated. The crude product was flash chromatographed (Merck silica gel) eluting with 1:1 ethyl acetate/hexane/1% acetic acid. The fractions containing clean desired product were combined, concentrated, azeotroped with ethyl acetate, and washed with water to remove the acetic acid. The organic layer was dried (sodium sulfate), filtered, and concentrated to give 2.70 g. of the title compound as a white crystalline product; m.p. 166°–168° C.; $[α]_D$=–153.6° (c=0.46, methylene chloride). TLC (1% acetic acid in 1:1 ethyl acetate/hexane) $R_f$=0.5.

b) N-[N-Phthalimido-3-(2-thienyl)-L-alanyl]-6-hydroxy-L-norleucine, methyl ester N-Methylmorpholine (1.51 ml., 14.5 mmol.) was added to a solution of 6-hydroxy-L-norleucine, methyl ester, hydrochloride (8.53 mmol.) in methylene chloride (34 ml)/dimethylformamide (9 ml.) at room temperature under argon. The resulting mixture was cooled to 0° C. and N-phthalimido-3-(2-thienyl)-L-alanine (2.57 g., 8.54 mmol.), hydroxybenzotriazole (1.19 g., 8.80 mmol.) and 1-ethyl-3-(3-dimethylaminopropyl)-carbodiimide (1.80 g., 9.4 mmol.) were added sequentially. After stirring at 0° C. for 30 minutes, the mixture was warmed to room temperature and stirred for 1.5 hours. The volatiles were evaporated and the residue was partitioned between ethyl acetate and water. The organic layer was washed successively with 0.5 N hydrochloric acid, water, saturated sodium bicarbonate, and brine, and the organic layer was dried (sodium sulfate), filtered, and concentrated. The residue was flash chromatographed (Merck silica gel) eluting with 2:1 ethyl acetate/hexane to give 3.13 g. of title compound as a white foam. TLC (5% acetic acid in ethyl acetate) $R_f$=0.68.

c) N-[N-Phthalimido-3-(2-thienyl)-L-alanyl]-6-oxo-L-norleucine, methyl ester

To a solution of 4-methylmorpholine N-oxide (1.12 g., 9.6 mmol., pre-dried over magnesium sulfate) and the product from part (b) (2.83 g., 6.37 mmol.) was added 4A molecular sieves and tetrapropyl ammoniumperruthenate (200 mg.). The resulting mixture was stirred for 2 hours at room temperature. The mixture was filtered through Celite and the volatiles were evaporated. The residue was flash chromatographed (Merck silica gel) eluting with 1:1 ethyl acetate/hexane to give 1.54 g. of title compound as white crystals; m.p. 125°–126° C.; $[α]_D$=–70.3° (c=0.46, methylene chloride). TLC (1:1, ethyl acetate/hexane) $R_f$=0.27.

d) (S)-1-[N-Phthalimido-3-(2-thienyl)-L-alanyl]-4-tetrahydro-2-pyridinecarboxylic acid, methyl ester Trifluoroacetic acid (73 µl) was added to a solution of the product from part (c) (1.53 g., 3.45 mmol.) in methylene chloride (36 ml.) at room temperature under argon. The mixture was gently refluxed for 3.5 hours. After cooling to room temperature, the mixture was washed with 50% saturated sodium bicarbonate, dried (sodium sulfate), filtered, and concentrated. The residue was flash chromatographed (Merck silica gel) eluting with 2:1 hexane/ethyl acetate to give 1.22 g. of title compound as a white foam. TLC (3:2, hexane/ethyl acetate) $R_f$=0.42.

e) [5S-[5α,8α,11aβ]]-5,6,9,10,11,11a-Hexahydro-6-oxo-5-phthalimido-4H,8H-pyrido[1,2-a]thieno[3,2-c]azepine-8-carboxylic acid, methyl ester The product from part (d) (1.16 g., 2.74 mmol.) was dissolved in methylene chloride (35 ml.) at room temperature under argon. Trifluoromethanesulfonic acid (1.82 ml.) was added and the resulting mixture was stirred for 1 hour. The mixture was poured into ice water and extracted with ethyl acetate. The organic layer was washed with brine, dried (sodium sulfate), filtered and concentrated to give 1.1 g of a yellow solid-like residue. The residue was dissolved in methylene chloride (8 ml.)/methanol (10 ml.) and cooled to 0° C. The mixture was treated with excess diazomethane for 5 minutes. The excess diazomethane was destroyed with acetic acid and the volatiles were removed. The yellow residue was flash chromatographed (Merck silica gel) eluting with 2:1 hexane/ethyl acetate to give 720 mg. of a white crystalline product. Recrystallization from hot ethyl acetate/hexane gave 670 mg. of analytically pure title compound; m.p. 163.5°–164° C.; $[\alpha]_D=-119.5°$ (c=0.43, methylene chloride). TLC (2:1, hexane/ethyl acetate) $R_f=0.15$.

f) [5S-[5α,8α,11aβ]]-5,6,9,10,11,11a-Hexahydro-5-amino-6-oxo-4H, 8H-pyrido[1,2-a]thieno[3,2-c]azepine-8-carboxylic, methyl ester The product from part (e) (670 mg., 1.58 mmol.) was suspended in methanol (8 ml.) at room temperature under argon. The mixture was treated with hydrazine monohydrate (0.17 ml.), became homogeneous, and was stirred for 16 hours. The mixture was filtered to remove the white precipitate and the filtrate was stripped, treated with methylene chloride, filtered and stripped again to give a white crystalline solid. The solid was recrystallized from hot ethyl acetate and hexane to give 372 mg. of title compound as white needle-like crystals; m.p. 151°–154° C.; $[\alpha]_D=-20-9°$ (c=0.47, methylene chloride). TLC (4% methanol in methylene chloride) $R_f=0.39$.

g) [5S-[5α(R*),8α,11aβ]]-5,6,9,10,11,11a-Hexahydro-5-[[2-(acetylthio)-1-oxo-3-phenylpropyl]amino]-6-oxo-4H, 8H-pyrido[1,2-a]thieno[3,2-c]azepine-8-carboxylic acid, methyl ester (S)-2-(Acetylthio)benzenepropionic acid, dicyclohexylamine salt (589 mg., 1.45 mmol.) was partitioned between ethyl acetate and 10% potassium bisulfate. The organic layer was washed with brine, dried (sodium sulfate), filtered, and concentrated to give (S)-2-(acetylthio) benzenepropanoic acid as an oil. The residue was dissolved in methylene chloride (15 ml.) at room temperature under argon. Following the addition of the product from part (f) (371 mg., 1.26 mmol.), the mixture was cooled to 0° C. and triethylamine (0.19 ml., 1.39 mmol.) was added. The resulting mixture was stirred for 5 minutes then benzotriazol-1-yloxytris (dimethylamino)phosphonium hexafluorophosphate (585 mg., 1.32 mmol.) was added. After being stirred at 0° C. for 1 hour, the reaction mixture was warmed to room temperature and was stirred for 16 hours. The volatiles were evaporated and the residue was dissolved in ethyl acetate and washed successively with 1 N hydrochloric acid, water, 50% saturated sodium bicarbonate, and brine. The organic layer was dried (sodium sulfate), filtered, and concentrated and the residue was flash chromatographed (Merck silica gel ) eluting with 3:2 hexane/ethyl acetate to give 508 mg. of the desired product as a white foam. TLC (1:1, ethyl acetate/hexane) $R_f=0.64$.

h) [5S-[5α(R*),8 α,11aβ]]-5,6,9,10,11,11a-Hexahydro-5-[(2-mercapto-1-oxo-3-phenylpropyl)amino]-6-oxo-4H,8H-pyrido[1,2-a]thieno[3,2-c]azepine-8-carboxylic acid A solution of the product from part (g) (496 mg., 1.1 mmol.) in methanol (10 ml., deoxygenated via argon bubbling) was cooled to 0° C. and treated with 1 N sodium hydroxide (8 ml., deoxygenated via argon bubbling). The resulting mixture was stirred under argon for 1 hour. The mixture was warmed to room temperature and stirred an additional 2.5 hours. The mixture was acidified with 10% potassium bisulfate and extracted with ethyl acetate. The organic layer was washed successively with water and brine, dried (sodium sulfate), filtered and concentrated to give a yellow oil. This residue was flash chromatographed (Merck silica gel) eluting with 1% acetic acid in 3:2 hexane/ethyl acetate. The fractions containing pure product were combined, concentrated, azeotroped with ethyl acetate, and washed with water to remove any acetic acid. The organic layer was dried (sodium sulfate), filtered and concentrated. The residue was taken up in ethyl acetate and triturated with hexane. The solvent was removed and the residue was slurried in hexane, stripped, and dried in vacuo to give 416 mg. of title product as a white powdery foam; $[\alpha]_D=+24.0°$ (c=0.52, methanol). TLC (2% acetic acid in ethyl acetate) $R_f=0.84$.

HPLC: YMC S-3 ODS (C- 18) 6.0×150 mm; 64% (10% water–90% methanol–0.2% phosphoric acid)/36% (90% water-10% methanol-0.2% phosphoric acid), flow rate= 1.5 ml/min, isocratic, detecting at 220 nm; $t_R=11.8$ min. indicates a purity of 95%.

Anal. calc'd. for $C_{22}H_{24}N_2O_4 \cdot 0.8$ water·0.25 hexane ·0.25 ethyl acetate C, 58.55; H, 6.24; N, 5.57; S, 12.76; Found C, 58.55; H, 5.88; N, 5.64; S, 12.56.

EXAMPLE 3

[5S-[5α(R*),8α,11aβ]]-5,6,9,10,11,11a-Hexahydro-5-[(2-mercapto-1-oxo-3-phenylpropyl)amino]-6-oxo-4H,8H-pyrido[1,2-a]thieno[2,3-c]azepine-8-carboxylic acid a) N-Phthalimido-3-(3-thienyl)-L-alanine 3-(3-Thienyl)-L-alanine (2.45 g., 14.3 mmol.) was suspended in water/p-dioxane (22 ml/11 ml.) at room temperature under argon. Sodium carbonate (1.52 g.) was added and the mixture was stirred until homogeneous. N-Carbethoxyphthalimide (3.14 g.) was added, and the resulting mixture was stirred for 3.0 hours and then cooled to 0° C. The pH was adjusted to 1.5 with 6 N hydrochloric acid and the mixture was extracted with ethyl acetate. The organic layer was washed successively with 10% potassium bisulfate and brine, dried (sodium sulfate), filtered, and concentrated. The crude product was flash chromatographed (Merck silica gel) eluting with 1:1 ethyl acetate/hexane/1% acetic acid. The fractions containing clean desired product were combined, concentrated, azeotroped with ethyl acetate, and washed with water to remove the acetic acid. The organic layer was dried (sodium sulfate), filtered, and concentrated to give 3.22 g. of title compound as a white crystalline product; m.p. 166°–168° C.; $[\alpha]_D=-146.8°$ (c=0.46, methylene chloride). TLC (1% acetic acid in 1:1 ethyl acetate/hexane) $R_f=0.31$.

b) N-[N-Phthalimido-3-(3-thienyl)-L-alanyl]-6-hydroxy-L-norleucine, methyl ester N-Methylmorpholine (1.89 ml., 18.12 mmol.) was added to a solution of 6-hydroxy-L-norleucine, methyl ester, hydrochloride (10.66 mmol.) in methylene chloride (41 ml.)/dimethylformamide (11 ml.) at room temperature under argon. The resulting mixture was cooled to 0° C. and N-phthalimido-3-(3-thienyl)-L-alanine (3.21 g., 10.66 mmol.), hydroxy-benzotriazole (1.48 g., 10.98 mmol.), and 1-ethyl-3-(3dimethylaminopropyl)carbodiimide (2.25 g., 11.73 mmol.) were added sequentially. After stirring at 0° C. for 30 minutes, the mixture was warmed to room temperature and stirred for 2 hours. The volatiles were evaporated and the residue was partitioned between ethyl acetate and water. The organic layer was washed successively with 0.5 N hydrochloric acid, water, saturated sodium bicarbonate, and brine, and the organic layer was dried (sodium sulfate), filtered, and concentrated. The residue was flash chromatographed (Merck silica gel) eluting with 4:1 ethyl acetate/hexane to give 3.8 g. of title compound as a white foam. TLC (ethyl acetate) $R_f=0.56$.

c) N-[N-Phthalimido-3-(3-thienyl)-L-alanyl]-6-oxo-L-norleucine, methyl ester

Oxalyl chloride (0.84 ml., 9.78 mmol.) was added to a flask containing methylene chloride (40 ml.) at −78° C.

under argon. Following the dropwise addition of dimethylsulfoxide (1.39 ml., 19.56 mmol.) in methylene chloride (2 ml.), the mixture was stirred for 20 minutes. A solution of the product from part (b) (3.62 g., 8.15 mmol.) in methylene chloride (20 ml.) was added, the mixture was stirred for 15 minutes, triethylamine (7.0 ml.) was added, and the mixture was stirred for 5 minutes. After warming to room temperature, the mixture was partitioned between ethyl acetate and 0.5 N hydrochloric acid and the organic layer was washed with brine, dried (sodium sulfate), filtered, and concentrated to obtain white crystals. The crystals were triturated with ethyl ether and collected by filtration to give 3.04 g. of title compound; m.p. 102°–104° C.; $[\alpha]_D = -58.0°$ (c=0.68, methylene chloride). TLC (ethyl acetate) $R_f$=0.83.

d) (S)-1-[N-Phthalimido-3-(3-thienyl)-L-alanyl]-4-tetrahydro-2-pyridinecarboxylic acid, methyl ester Trifluoroacetic acid (0.15 ml.) was added to a solution of the product from part (c) (3.02 g., 6.83 mmol.) in methylene chloride (70 ml.) at room temperature under argon. The mixture was gently refluxed for 3 hours. After cooling to room temperature, the mixture was washed with 50% saturated sodium bicarbonate, dried (sodium sulfate), filtered, and concentrated. The residue was flash chromatographed (Merck silica gel) eluting with 3:2 hexane/ethyl acetate to give 2.49 g. of title compound as a white foam. TLC (3:2, hexane/ethyl acetate) $R_f$=0.44.

e) [5S-[5α,8α,11aβ]]-5,6,9,10,11,11a-Hexahydro-6-oxo-5-phthalimido-4H,8H-pyrido[1,2-a]thieno[2,3-c]azepine-8-carboxylic acid, methyl ester The product from part (d) (2.29 g., 5.40 mmol.) was dissolved in methylene chloride (70 ml.) at room temperature under argon. Trifluoromethanesulfonic acid (3.6 ml.) was added and the resulting mixture was stirred for 0.5 hour. The mixture was poured into ice water and extracted with ethyl acetate. The organic layer was washed with brine, dried (sodium sulfate), filtered and concentrated to give a dark orange oil. The residue was dissolved in methylene chloride (15 ml.)/methanol (20 ml.) and cooled to 0° C. The mixture was treated with excess diazomethane for 5 minutes. The excess diazomethane was destroyed with acetic acid and the volatiles were removed. The residue was flash chromatographed (Merck silica gel) eluting with 1:1 hexane/ethyl acetate to give 441 mg. of title compound as a white crystalline product; m.p. 132°–134° C.; $[\alpha]_D = -87.4°$ (c=0.47, methylene chloride). TLC (1:1, hexane/ethyl acetate) $R_f$=0.5.

f) [5S-[5α,8α,11aβ]]-5,6,9,10,11,11a-Hexahydro-5-amino-6-oxo-4H,8H-pyrido[1,2-a]thieno[2,3-c]azepine-8-carboxylic acid, methyl ester The product from part (e) (370 mg., 0.87 mmol.) was suspended in methanol (8 ml.) at room temperature under argon. After methylene chloride (4 ml.) was added to effect a homogeneous mixture, the mixture was treated with hydrazine monohydrate (0.09 ml., 1.92 mmol., 2.2 equiv.) and was stirred for 1.5 hours. The volatiles were evaporated and the residue was chased with toluene (×2). The residue was redissolved in methanol and stirred at room temperature for 72 hours. The mixture was filtered to remove the white precipitate and the filtrate was stripped, treated with methylene chloride, filtered and stripped again to give 300 mg. of title product as a yellow oil. TLC (4% methanol in methylene chloride) $R_f$=0.63.

g) [5S-[5α(R*),8α,11aβ]]-5,6,9,10,11,11a-Hexahydro-5-[[2-(acetylthio)-1-oxo-3-phenylpropyl]amino]-6-oxo-4H,8H-pyrido[1,2-a]thieno[2,3-c]azepine-8-carboxylic acid, methyl ester (S)-2-(Acetylthio)benzenepropanoic acid, dicyclohexylamine salt (406 mg., 1.0 mmol.) was partitioned between ethyl acetate and 10% potassium bisulfate. The organic layer was washed with brine, dried (sodium sulfate), filtered, and concentrated to give (S)-2-(acetylthio)benzenepropanoic acid as an oil. The residue was dissolved in methylene chloride (10 ml.) at room temperature under argon. Following the addition of the product from part (f) (0.87 mmol.), the mixture was cooled to 0° C. and triethylamine (0.13 ml., 0.96 mmol.) was added. The resulting mixture was stirred for 5 minutes then benzotriazol-1-yloxytris(dimethylaminopropyl)-phosphonium hexafluorophosphate (403 mg., 0.91 mmol.) was added. After being stirred at 0° C. for 1 hour, the reaction mixture was warmed to room temperature and was stirred for 16 hours. The volatiles were evaporated and the residue was dissolved in ethyl acetate and washed successively with 1 N hydrochloric acid, water, 50% saturated sodium bicarbonate, and brine. The organic layer was dried (sodium sulfate), filtered, and concentrated and the residue was flash chromatographed (Merck silica gel) eluting with 3:2 hexanemethyl acetate to give 367 mg. of the desired product as a yellow oil. TLC (1:1, ethyl acetate/hexane) $R_f$=0.52.

h) [5S-[5α(R*),8α,11aβ]]-5,6,9,10,11,11a-Hexahydro-5-[(2-mercapto-1-oxo-3-phenylpropyl)amino]-6-oxo-4H,8H-pyrido[1,2-a]thieno[2,3-c]azepine-8-carboxylic acid A solution of the product from part (g) (365 mg., 0.78 mmol.) in methanol (8 ml., deoxygenated via argon bubbling) was cooled to 0° C. and treated with 1 N sodium hydroxide (6 ml., deoxygenated via argon bubbling). The resulting mixture was stirred under argon for 0.5 hour. The mixture was warmed to room temperature and stirred an additional 4.5 hours. The mixture was acidified with 10% potassium bisulfate and extracted with ethyl acetate. The organic layer was washed successively with water and brine, dried (sodium sulfate), filtered and concentrated to give a yellow oil. This residue was flash chromatographed (Merck silica gel) eluting with 1% acetic acid in 3:2 hexane/ethyl acetate. The fractions containing pure product were combined, concentrated, azeotroped with ethyl acetate, and washed with water to remove any acetic acid. The organic layer was dried (sodium sulfate), filtered and concentrated. The residue was taken up in ethyl acetate and triturated with hexane. The solvent was removed and the residue was slurried in hexane, stripped, and dried in vacuo to give 310 mg. of title compound as a white powdery foam; $[\alpha]_D = +29.8°$ (c=0.38, methylene chloride). TLC (2% acetic acid in ethyl acetate) $R_f$=0.82.

HPLC: YMC S-3ODS (C-18) 6.0×150 mm; 65% (10% water-90% methanol-0.2% phosphoric acid)/35% (90% water-10% methanol-0.2% phosphoric acid), flow rate= 1.5 ml/min, isocratic, detecting at 220 nm; $t_r$=11.9 min indicates a purity of 99.2%

Anal. calc'd. for $C_{22}H_{24}N_2O_4S_2 \cdot 1.0 H_2O$: C, 57.05; H, 5.67; N, 6.05; S, 13.84;

Found C, 57.15; H, 5.56; N, 5.95; S, 13.30.

EXAMPLE 4

1000 tablets each containing the following ingredients:

| | |
|---|---|
| [5S-[5α(R*),8α,11aβ]]-5,6,9,10,11,11a-Hexahydro-5-[(2-mercapto-1-oxo-3-phenylpropyl)amino]-6-oxo-4H,8H-pyrido[1,2-a]thieno[2,3-c]azepine-8-carboxylic acid | 200 mg. |
| Cornstarch | 100 mg. |
| Gelatin | 20 mg. |
| Avicel (microcrystalline cellulose) | 50 mg. |
| Magnesium stearate | 5 mg. |
| | 375 mg. | are prepared from sufficient bulk quantities by mixing the product of Example 3 and cornstarch with an aqueous solution of the gelatin. The mixture is dried and ground to a fine powder. The Avicel and then the magnesium stearate are admixed with granulation. The mixture is then compressed in a tablet press to form 1000 tablets each containing 200 mg. of active ingredient.

In a similar manner, tablets containing 200 mg. of the product of Examples 1 or 2 can be prepared.

Similar procedures can be employed to form tablets or capsules containing from 50 mg. to 500 of active ingredient.

What is claimed is:

1. A compound of the formula

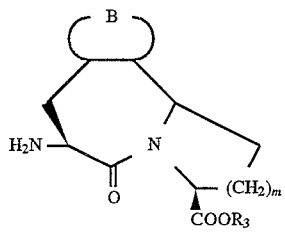

wherein m is one or two;

$R_3$ is hydrogen, alkyl, substituted alkyl, aryl-$(CH_2)_p$-, or substituted aryl-$(CH_2)_p$-;

p is zero or an integer from 1 to 6;

represents an aromatic heteroatom containing ring selected from the group consisting of

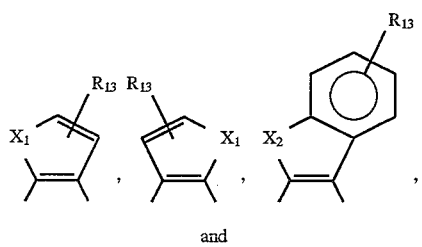

and

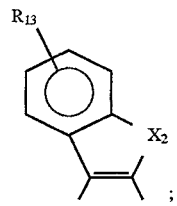

$X_1$ is S or NH;

$X_2$ is S, O, or NH; and $R_{13}$ is hydrogen, lower alkyl, lower alkoxy, lower alkylthio, chloro, bromo, fluoro, trifluoro-methyl, amino, —NH(lower alkyl), —N(lower alkyl)$_2$, or hydroxy;

the term "alkyl" refers to straight or branched chain radicals of one to seven carbon atoms;

the term "substituted alkyl" refers to such straight or branched chain radicals of 1 to 7 carbons wherein one or more hydrogens have been replaced by a hydroxy, amino, halo, trifluoromethyl, cyano, —NH(lower alkyl), —N(lower alkyl)$_2$, lower alkoxy, lower alkylthio, or carboxy;

the term "aryl" refers to phenyl, 1-naphthyl, and 2-naphthyl;

the term "substituted aryl" refers to phenyl, 1-naphthyl, and 2-naphthyl having a substituent selected from lower alkyl, lower alkoxy, lower alkylthio, halo, hydroxy, trifluoromethyl, amino, —NH(lower alkyl), and —N(lower alkyl)$_2$, and di- and tri-substituted phenyl, 1-naphthyl, and 2-naphthyl wherein said substituents are selected from methyl, methoxy, methylthio, halo, hydroxy, and amino;

the term "lower alkyl" refers to straight or branched radicals of 1 to 4 carbons;

the terms "lower alkoxy" and "lower alkylthio" refer to such lower alkyl groups as defined above attached to an oxygen sulfur; and the term "halo" refers to chloro, bromo, fluoro, and iodo.

2. A compound of claim 1 wherein:

m is one or two;

$R_3$ is hydrogen, lower alkyl, or aryl-(CH2)$_p$-;

p is zero or an integer from 1 to 6; and

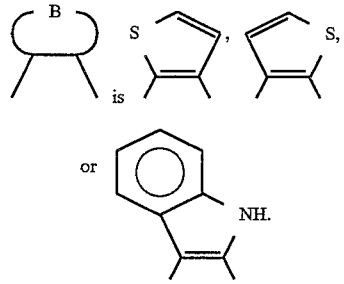

3. The compound of claim 2, [4S-[4α, 7α, 13bβ]]-1,3,4,6,7,8,13,13b-octahydro-7-amino-6-oxo-2H-pyrido[1'2':1,2]azepino[3,4-b]indole-4-carboxylic acid, methyl acid.

4. The compound of claim 2, [5S-[5α,8α,11aβ]]-5,6,9,10,11,11a-hexahydro-7-amino-6-oxo-4H,8H-pyrido[1,2-a]thieno[3,2-c]azepine-8-carboxylic acid, methyl ester.

5. The compound of claim 2, [5S-[5α,8α,11aβ]]-5,6,9,10,11,11a-hexahydro-7-amino-6-oxo-4H,8H-pyrido[1,2-a]thieno[2,3-c]azepine-8-carboxylic acid, methyl ester.

* * * * *